United States Patent [19]
Takeda et al.

[11] Patent Number: 6,083,968
[45] Date of Patent: Jul. 4, 2000

[54] TRIAZOLE DERIVATIVE OR SALT THEREOF, PREPARATION PROCESS THEREOF AND PHARMACEUTICAL CONTAINING SAID COMPOUND AS AN EFFECTIVE INGREDIENT

[75] Inventors: Sunao Takeda, Ichihara; Yasushi Kaneko, Narita; Minoru Tokizawa, Narita; Hiromichi Eto, Narita; Kazuya Ishida, Narita; Kazunori Maebashi, Narashino; Masaru Matsumoto, Inba-gun; Takemitsu Asaoka, Narita; Susumu Sato, Chiba, all of Japan

[73] Assignee: SSP Co., Ltd., Tokyo, Japan

[21] Appl. No.: 09/207,924

[22] Filed: Dec. 9, 1998

[30] Foreign Application Priority Data

Dec. 26, 1997 [JP] Japan .................................. 9-359202
Jul. 1, 1998 [JP] Japan .................................. 10-186198

[51] Int. Cl.$^7$ .................................................. A01N 43/80
[52] U.S. Cl. ........................................ 514/383; 548/268.6
[58] Field of Search ........................... 514/383; 548/268.6

[56] References Cited

U.S. PATENT DOCUMENTS 5,945,438   8/1999   Tokizawa et al. ...................... 514/383

FOREIGN PATENT DOCUMENTS

| | | |
|---|---|---|
| 113640 | 12/1983 | European Pat. Off. . |
| 0 140 154 | 5/1985 | European Pat. Off. . |
| 0 435 081 | 7/1991 | European Pat. Off. . |
| 0 473 387 | 3/1992 | European Pat. Off. . |
| 780380 | 6/1997 | European Pat. Off. . |
| 0 814 079 | 12/1997 | European Pat. Off. . |

OTHER PUBLICATIONS

Hiroshi Miyauchi, et al., Bioorganic & Medicinal Chemistry Letters, vol. 5, No. 9, pp. 933–936, "Synthesis and Antifungal Activities of Optically Active Isomers of SM–8668", May 4, 1995.

Hiroshi Miyauchi, et al., Bioorganic & Medicinal Chemistry Letters, vol. 5, No. 14, pp. 1479–1482, "Structure–Activity Relationships of Sulfur–Containing Triazole Antifungals", Jul. 20, 1995.

*Primary Examiner*—Patricia L. Morris
*Attorney, Agent, or Firm*—Oblon, Spivak, McClelland, Maier & Neustadt, P.C.

[57] ABSTRACT

Described is a triazole derivative represented by the formula (1):

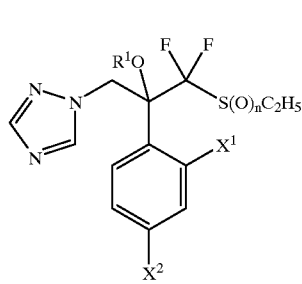

wherein $R^1$ represents a hydrogen atom, a lower alkyl group or an aralkyl group, $X^1$ and $X^2$ are the same or different and each independently represents a hydrogen atom, a halogen atom or a halogenoalkyl and n stands for an integer of 0 to 2, or salt thereof; a preparation process of said compound and a pharmaceutical comprising said compound as an effective ingredient.

The compound as described above has high antimycotic activity and is useful for the prevention and treatment of mammalian mycotic infections.

3 Claims, No Drawings

TRIAZOLE DERIVATIVE OR SALT THEREOF, PREPARATION PROCESS THEREOF AND PHARMACEUTICAL CONTAINING SAID COMPOUND AS AN EFFECTIVE INGREDIENT

BACKGROUND OF THE INVENTION

1. Field of the Invention

This invention relates to a triazole derivative or salt thereof which has excellent antimycotic action and high safety, an intermediate for preparing said compound and a pharmaceutical comprising said compound as an effective ingredient.

2. Description of the Related Art

Mycosis can be classified into two types, that is, superficial mycosis represented by various trichophytosis, marginated eczema, psoriasis, cutaneous candidiasis or the like and deep seated mycosis represented by mycotic meningitis, mycotic infectious disease of respiratory organ, fungemia, mycosis of urinary tract or the like. Of these, deep seated mycosis such as candidiasis or aspergillosis tends to show a marked increase in recent days owing to the frequent use of an anticancer chemotherapeutic agent or immunosuppressive agent or lowering in the bioimmunology due to HIV infection or the like. There is accordingly a demand for a pharmaceutical efficacious against fungi causing such diseases.

As pharmaceuticals effective against Aspergillus spp. and Candida spp., Amphotericin B and azole base compounds such as Fluconazole and Itraconazole are conventionally known, but not so many pharmaceuticals have been commercially available yet. In addition, the above-exemplified pharmaceuticals involve problems in safety and antimycotic action. There is accordingly a demand for an antimycotic effective against Aspergillus spp. and Candida spp. Now, more effective azole base compounds are under development. For example, as a compound having a difluoromethylene group, those described in Japanese Patent Application Laid-Open Nos. 163374/1984, 163269/1993 and 227531/1997 are known. As an azole base compound having a substituted tertiary hydroxyl group, cyclic compounds as described in Japanese Patent Application Laid-Open Nos. 217778/1996 and 333367/1996, acyl compounds as described in Japanese Patent Application Laid-Open Nos. 104676/1996 and 183769/1997, and the like are known but they are not fully satisfactory.

SUMMARY OF THE INVENTION

Accordingly, an object of the present invention is to provide a compound which has high safety and has antimycotic activity effective against Aspergillus spp. and Candida spp.

With the forgoing in view, the present inventors synthesized a number of triazole derivatives and salts thereof and carried out an investigation on their antimycotic activity effective against Aspergillus spp. and Candida spp. As a result, it has been found that an ethylthio- or ethylsul-fonyl-containing triazole derivative represented by the below-described formula (1) and a salt thereof are superior in antimycotic activity against fungi including Aspergillus spp. and Candida spp. and also in safety to the analogous compounds which have been known to date, leading to the completion of the present invention.

In one aspect of the present invention, there is thus provided a triazole derivative represented by the following formula (1):

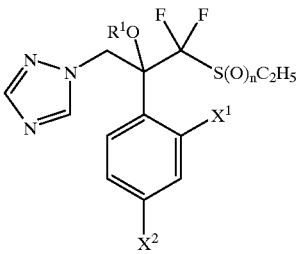

(1)

wherein $R^1$ represents a hydrogen atom, lower alkyl group or aralkyl group, $X^1$ and $X^2$ are the same or different and each independently represents a hydrogen atom, a halogen atom or a halogenoalkyl group, n stands for an integer of 0 to 2, or salt thereof; an intermediate for preparing said compound; and a preparation process of these compounds.

In another aspect of the present invention, there is also provided a pharmaceutical comprising the triazole derivative (1) or salt thereof as an effective ingredient.

In a further aspect of the present invention, there is also provided a pharmaceutical composition comprising the triazole derivative (1) or salt thereof and a pharmacologically acceptable carrier.

In a still further aspect of the present invention, there is also provided the use of the triazole derivative (1) or salt thereof as a pharmaceutical.

In a still further aspect of the present invention, there is also provided a treating method of mycotic infections, which comprises administering to a patient the triazole derivative (1) or salt thereof.

The triazole derivative or salt thereof according to the present invention has strong antimycotic activity, and an antimycotic comprising such compound as an effective ingredient is useful for the prevention and treatment of mycotic infections of mammary animals including human.

BRIEF DESCRIPTION OF THE PREFERRED EMBODIMENTS

In the triazole derivative of the present invention, examples of the lower alkyl group represented by $R^1$ in the formula (1) include linear or branched $C_{1-6}$ alkyl groups. Specific examples include methyl, ethyl, n-propyl, i-propyl, n-butyl, i-butyl, sec-butyl, t-butyl, n-pentyl i-pentyl and n-hexyl. As the aralkyl group represented by $R^1$, $C_{7-10}$ aralkyl groups are preferred, with phenyl-$C_{1-4}$ alkyl groups being more preferred. Specific examples include benzyl and phenethyl and phenylpropyl. As $R^1$, methyl and benzyl groups are preferred. Examples of the halogen atom represented by $X^1$ or $X^2$ include fluorine, chlorine, bromine and iodine atoms, with the fluorine and chlorine atoms being particularly preferred. Examples of the halogenoalkyl group include the above-exemplified $C_{1-6}$ alkyl groups substituted by the above-exemplified halogen atom. Among them, a perfluoroalkyl group is preferred, with trifluoromethyl and pentafluoroethyl groups being particularly preferred and trifluoromethyl group being more preferred. The number n of oxygen atoms stands for an integer of 0 to 2, with 0 and 2 being preferred.

No particular limitation is imposed on the salt of the triazole derivative (1) of the present invention insofar as it is a pharmacologically acceptable salt. Examples include acid addition salts such as hydrochlorides, nitrates, hydrobromides, p-toluenesulfonates, methanesulfonates, fumarates, succinates and lactates.

The triazole derivative (1) or salt thereof according to the present invention has stereoisomers based on its asymmetric carbon and sulfoxide. The present invention therefore embraces any of such isomers and isomer mixtures such as racemic modifications. The triazole derivative (1) or salt thereof may exist in the form of a solvate typified by a hydrate. The present invention also embraces solvates of these compounds.

The triazole derivative (1) of the present invention can be prepared, for example, in accordance with the reaction scheme described below:

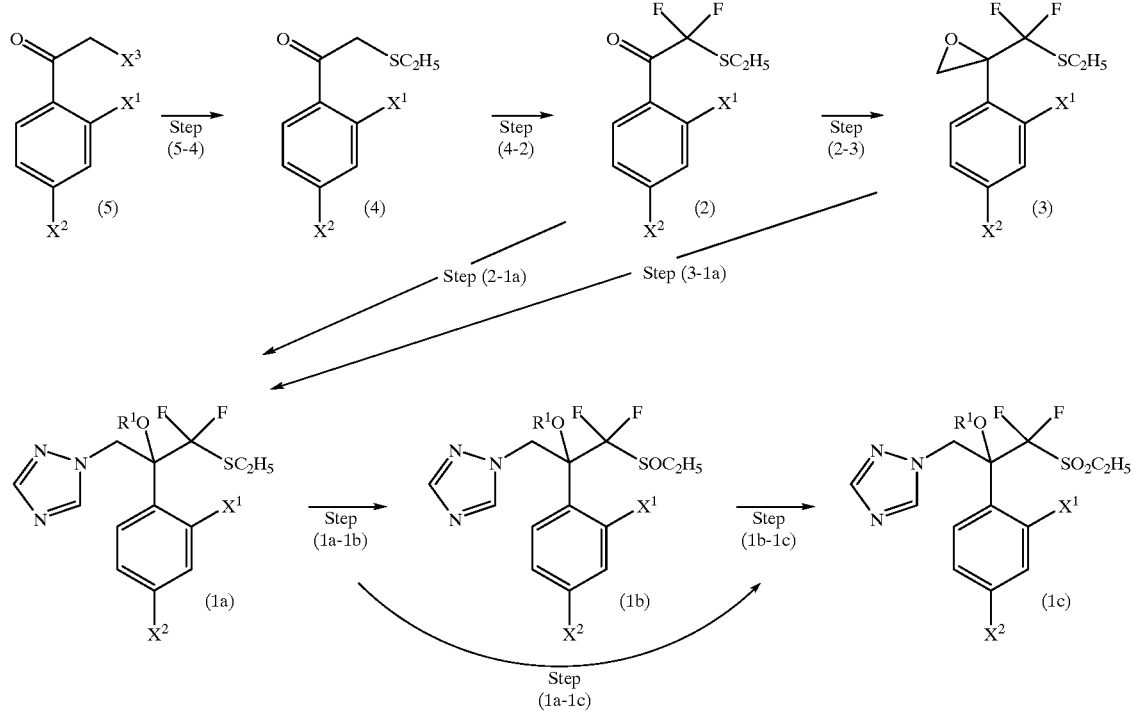

wherein $R^1$, $X^1$ and $X^2$ have the same meanings as defined above and $X^3$ represents a halogen atom.

Described specifically, Compound (1a), that is, a compound of the formula (1) wherein n stands for 0 can be prepared by introducing an ethylthio group into a 2-haloacetophenone derivative (5) which is a known compound, difluorinating the resulting ethylthio compound (4) into Compound (2) and directly introducing a triazole methyl group into Compound (2) or first introducing an epoxymethylene group into Compound (2) to obtain Compound (3) and then introducing a triazole group into Compound (3). The $R^1$ of the resulting Compound (1a) can be alkylated or aralkylated as desired. By the oxidation of Compound (1a), Compound (1b), that is, a compound of the formula (1) wherein n stands for 1 or Compound (1c), that is, a compound of the formula (1) wherein n stands for 2 can be prepared. Alternatively, Compound (1c) can be prepared by the oxidation of Compound (1b).

In the above preparation process, a 2,2-difluoro-2-ethylthioacetophenone derivative represented by the formula (2) and an oxirane derivative represented by the formula (3) are novel compounds synthesized by the present inventors and are useful as an intermediate for the synthesis of a triazole derivative (1).

The present invention will next be described more specifically in accordance with the above steps.

STEP (5-4):

Compound (4) can be prepared by introducing an ethylthio group into Compound (5).

In Compound (5) employed as a starting material, examples of $X^3$ in the formula (5) include fluorine, chlorine and bromine atoms. Among them, chlorine and bromine atoms are preferred. Compound (5) which contains as $X^3$ a fluorine, chlorine or bromine atom and as $X^1$ and $X^2$ a fluorine atom are, for example, commercially available from Aldrich Chemical Co., Inc.

Compound (4) can be prepared by reacting Compound (5) with ethyl mercaptan in the presence of a base. Examples of the reaction solvent include alcoholic solvents such as methanol and ethanol, N,N-dimethylformamide, 1,4-dioxane and tetrahydrofuran, with the alcoholic solvents, particularly, methanol being preferred. As a base, sodium carbonate, potassium carbonate, sodium hydroxide, potassium hydroxide, sodium hydride, potassium hydride, sodium methoxide, sodium ethoxide, pyridine, triethylamine or the like is usable. Among them, potassium carbonate is preferred.

STEP (4-2)

Compound (2) can be prepared by reacting Compound (4) with a fluorinating reagent in a solvent.

Examples of the fluorinating agent include fluorine gas, perchloryl fluoride, potassium fluoride, spray-dried potassium fluoride, freeze-dried potassium fluoride, tetraalkylammonium fluoride, tris(dimethylamino)sulfa-(trimethylsilyl) difluoride, N-fluoropyridone, N-fluoro-N-alkyl-arenesulfonamide, N-fluoroquinuclidinium salt, N-fluoroperfluoroalkyl sulfonimide, N-fluorosaltum, fluorinated xenon, N-fluoropyridinium salt and N-fluoropyridinium sulfonate. Examples of the commercially available fluorinating reagent include "Onoda Fluorinates FP-T300, FP-T500, FP-T700, FP-B300, FP-B500, FP-B700 and FP-B800" (trade names; products of Chichibu Onoda Co., Ltd.) and "MEC-01, MEC-02, MEC-03, MEC-04 and MEC-05" (trade names; products of Daikin Industries, Ltd.). It is preferred to use the fluorinating reagent in an amount of 2 to 20 equivalents per mole of Compound (4).

Illustrative of the reaction solvent include 1,2-dichloroethane, 1,1,2-trichloroethane, chloroform, methylene chloride, diethyl ether, ethyl acetate and tetrahydrofuran. Among them, 1,1,2-trichloroethane is preferred. The reaction temperature is −78° C. to the boiling point of a solvent, with 80 to 100° C. being preferred.

To improve the yield of the compound, a Lewis acid or a base can be used. Exemplary Lewis acids include aluminum chloride, zinc chloride and tin chloride, while exemplary bases include sodium hydroxide, potassium hydroxide, barium hydroxide, sodium carbonate, potassium carbonate, sodium hydride, potassium tert-butoxide, lithium diisopropylamide and potassium hexamethyldisilazane.

STEP (2-1a):

Direct synthesis from Compound (2) to Compound (1a) is carried out by reacting 1 mole of Compound (2) with 1 to 5 moles of an epoxymethylene-introducing agent and 1 to 4 moles of 1,2, 4-triazole or alkaline metal salt thereof at −100° C. to room temperature or boiling point of the solvent for 1 to 30 hours in a solvent. Examples of the epoxymethylene-introducing agent include trimethylsulfoxonium iodide and trimethylsulfonium iodide. Examples of the base include sodium hydroxide, potassium hydroxide, barium hydroxide, sodium methoxide, sodium carbonate, potassium carbonate and sodium hydride, with potassium hydroxide being particularly preferred. As the solvent, methanol, ethanol, isopropanol, n-butanol, sec-butanol, t-butanol and the like are preferred.

STEP (2-3)

Compound (1a) Can be Prepared Via Compound (3).

Compound (3) can be obtained by reacting Compound (2) with 1 to 2 equivalents of an epoxymethylene-introducing agent such as trimethylsulfoxonium iodide or trimethylsulfonium iodide in the presence of 1 to 5 equivalents of an alkali. Dimethylsulfoxide, tetrahydrofuran or the like can be suitably used as a solvent. Examples of the base include sodium hydroxide, potassium hydroxide, barium hydroxide, sodium methoxide, sodium ethoxide, sodium carbonate, potassium carbonate and sodium hydride, with sodium hydride and sodium methoxide being particularly preferred. The reaction temperature preferably ranges from −100° C. to the boiling point of the solvent, with a range of from −40 to 50° C. being particularly preferred.

STEP (3-1a):

Compound (1a) containing as $R^1$ a hydrogen atom can be prepared by reacting Compound (3) with 1,2, 4-triazole or alkali metal salt thereof in a solvent in the presence of a base. Preferred examples of the solvent include N,N-dimethylformamide, acetonitrile, N,N-dimethylacetamide and dimethylsulfoxide. Examples of the base include sodium hydroxide, potassium hydroxide, barium hydroxide, sodium carbonate, potassium carbonate and tert-butoxy potassium. The reaction temperature preferably ranges from 0° C. to the boiling point of the solvent, with a range of 20 to 60° C. being particularly preferred.

Compound (1a) containing as $R^1$ a hydrogen atom can be converted into that containing as $R^1$ a lower alkyl or aralkyl group by alkylating or aralkylating the tertiary hydroxyl group in the presence of a base as desired. Examples of the alkyl halide to be used for the alkylation include methyl iodide, ethyl iodide, propyl iodide and benzyl chloride. Examples of the base include sodium hydroxide, potassium hydroxide, barium hydroxide, sodium carbonate, potassium carbonate and sodium hydride. Examples of the solvent include alcoholic solvents such as methanol and ethanol, nonaqueous polar solvents such as N,N-dimethylformamide (DMF) and ether solvents such as 2,4-dioxane and tetrahydrofuran (THF), with DMF being particularly preferred. The reaction temperature preferably ranges from −40° C. to the boiling point of the solvent, with 0 to 20° C. being particularly preferred.

STEP (1a–1c):

Compound (1c) can be prepared by adding at least 2 equivalents, preferably 2.2 to 2.3 equivalents of an oxidizing agent to Compound (1a). Examples of the oxidizing agent include m-chloroperbenzoic acid, aqueous hydrogen peroxide, peracetic acid, tetrapropylammonium perruthenate, osmium tetraoxide, potassium permanganate and oxone. Illustrative of the solvent include chloroform, dichloromethane, acetic acid, methanol, water, acetonitrile and carbon tetrachloride, and mixtures thereof. The reaction temperature is preferably −40° C. to the boiling point of the solvent, with 0 to 50° C. being particularly preferred. To improve the yield, ruthenium trichloride, selenium dioxide, sodium tungstate, sodium molybdate and vanadium oxide may be used as a catalyst.

STEP (1a–1b) and STEP (1b–1c):

Compound (1b) can be prepared by adding 1 to 2 equivalents, preferably 1.2 equivalents of an oxidizing agent to Compound (1a). Examples of the oxidizing agent include m-chloroperbenzoic acid, aqueous hydrogen peroxide, peracetic acid, tetrapropylammonium perruthenate, osmium tetraoxide, potassium permanganate and oxone. Illustrative of the solvent include chloroform, dichloromethane, acetic acid, methanol, water, acetonitrile and carbon tetrachloride, and mixtures thereof. The reaction temperature is preferably −40° C. to the boiling point of the solvent, with 0 to 50° C. being particularly preferred. To improve the yield, ruthenium trichloride, selenium dioxide, sodium tungstate, sodium molybdate and vanadium oxide may be used as a catalyst. Step (1b–1c) can be carried out similarly.

Compounds (1a), (1b) and (1c) each has enantiomers based on its asymmetric carbon atom. Such an optically active substance can be prepared by separating using a column for separation of an optical isomer. Examples of the optically active stationary phase include synthetic optically active polymers, natural high molecules and amino acid metal complexes. Among them, a cellulose-derivative-coated silica gel is preferred. As a column filled with this cellulose-derivative-coated silica gel, commercially-available products such as CHIRALCEL OD and CHIRALPAK AS (each, trade name; product of Daicel Chemical Industries, Ltd.) can be used, with CHIRALCEL OD being particularly preferred. As chromatography, liquid chromatography is preferred. In this case, hexane—ethanol, hexane—isopropyl alcohol can be used as an eluent as a mobile phase.

The optically active substance can also be prepared by optical resolution. Examples of the reagent for optical resolution include optically active camphor-sulfonic acid or salt thereof which may be substituted with a halogen atom. Specific examples include (+)-camphor-10-sulfonic acid, (−)-camphor-10-sulfonic acid, (+)-3-bromocamphor-8-sulfonic acid, (−)-3-bromocamphor-8-sulfonic acid, (+)-3-bromocamphor-10-sulfonic acid, (−)-3-bromocamphor-10-sulfonic acid, ammonium (+)-3-bromocamphor-8-sulfonate and ammonium (−)-3-bromocamphor-7-sulfonate. Among them, (+)-3-bromocamphor-8-sulfonic acid, (−)-3-bromocamphor-8-sulfonic acid, ammonium (+)-3-bromocamphor-8-sulfonate and ammonium (−)-3-bromocamphor-7-sulfonate are particularly preferred.

No particular limitation is imposed on the isolation means of a target product from the reaction mixture available by each of the above-described reactions. The target product can be isolated, for example, by recrystallization, various types of chromatography or the like. Moreover, the target compound can be converted into a desired salt in a conventional manner.

From the invention compound, a pharmaceutical, particularly, an antimycotic can be obtained in various dosage forms such as tablets, granules, powders, capsules, suspensions, injections, suppositories and external preparations. In this case, it is possible to prepare the pharmaceutical by incorporating therein a pharmacologically acceptable carrier. Described specifically, a solid preparation can be prepared in a conventional manner by adding to the invention compound (1) an excipient and, if necessary, a binder, disintegrator, extender, coating agent, sugar-coating agent and/or the like. An injection may be prepared by dissolving, dispersing or emulsifying the invention compound (1) in an aqueous carrier such as distilled water for injection to form an injection liquid in advance or to prepare powder for injection and dissolve it upon use. Examples of the administration method of the injection include intravenous administration, intraarterial administration, intraperitoneal administration, subcutaneous administration and instillation.

The dose of the invention compound or salt thereof as a pharmaceutical differs depending on various factors such as symptoms, weight, age or sex of the patient to be administered or administration route. When used as an antimycotic, the pharmaceutical is used in an amount of 0.1 to 1000 mg/day, preferably 1 to 300 mg/day per adult in terms of the invention compound (1) or salt thereof. It is possible to add the above-described amount once a day or 2 to 4 portions a day.

EXAMPLES

The present invention will hereinafter be described in detail by referential examples and examples. It should however be borne in mind that the present invention will not be limited to or by the following examples.

Referential Example 1

Synthesis of 2', 4'-difluoro-2-(ethylthio) acetophenone [Compound (4-1)]

To a solution of 2-chloro-2', 4'-difluoroacetophenone (10 g, 0.053 mol) and ethyl mercaptan (3.6 g, 0.058 mol) in methanol (200 ml), potassium carbonate (8.8 g, 0.064 mol) was added under ice cooling, followed by stirring at room temperature for 1.5 hours. After the completion of the reaction, the solvent was distilled off under reduced pressure. Water was added to the residue, followed by extraction with ether. The extract was washed successively with water and saturated saline and dried over magnesium sulfate. The solvent was then distilled off under reduced pressure. The resulting oil was distilled under reduced pressure (bp: 115 to 118° C., 2 mmHg), whereby 2', 4'-difluoro-2-(ethylthio) acetophenone (11.4 g, yield: 99.9%) was obtained as a colorless oil.

$^1$H-NMR(CDCl$_3$, δ):

1.24(3H,t,J=7 Hz), 2.51(2H,q,J=7 Hz), 3.77(2H,d,J=2 Hz), 6.75–7.09(2H,m), 7.86–8.13(1H,m).

Referential Example 2

Synthesis of 2-ethylthio-4'-fluoroacetophenone [Compound (4-2)]

In a similar manner to Referential Example 1 except for the use of 2-chloro-4'-fluoroacetophenone instead of 2-chloro-2', 4'-difluoroacetophenone, 2-ethylthio-4'-fluoroacetophenone was obtained as a colorless oil.

$^1$H-NMR(CDCl$_3$, δ):

1.27(3H,t,J=7.2 Hz), 2.58(2H,q,J=7.2 Hz), 3.77(2H,s), 7.00–7.40(2H,m), 7.90–8.10(2H,m).

Referential Example 3

Synthesis of 2-ethylthio-4'-trifluoromethylacetophenone [Compound (4-3)]

In a similar manner to Referential Example 1 except for the use of 2-bromo-4'-trifluoromethylacetophenone instead of 2-chloro-2', 4'-difluoroacetophenone, 2-ethylthio-4'-trifluoromethylacetophenone was obtained as a colorless oil.

$^1$H-NMR(CDCl$_3$, δ):

1.27(3H,t,J=7.5 Hz), 2.57(2H,q,J=7.5 Hz), 3.80(2H,s), 7.74(2H,d,J=8.4 Hz), 8.10(2H,d,J=8.4 Hz).

Referential Example 4

Synthesis of 2', 4'-dichloro-2-(ethylthio) acetophenone [Compound (4-4)]

In a similar manner to Referential Example 1 except for the use of 2,2', 4'-trichloroacetophenone instead of 2-chloro-2', 4'-difluoroacetophenone, 2', 4'-dichloro-2-(ethylthio) acetophenone was obtained as a colorless oil.

$^1$H-NMR(CDCl$_3$, δ)

1.25(3H,t,J=7.3 Hz), 2.55(2H,q,J=7.3 Hz), 3.80(2H,s), 7.20–7.70(3H,m)

Example 1

Synthesis of 2-ethylthio-2,2,2', 4'-tetrafluoroacetophenone [Compound (2-1)

To a solution of 2', 4'-difluoro-2-(ethylthio)acetophenone (11.4 g, 0.053 mol) in 1,1,2-trichloroethane (100 ml), N-fluoro-4-methylpyridinium-2-sulfonate ("MEC-02", trade name; Daikin Kogyo Co., Ltd.) (24 g, 0.127 mol) was added in portions at an internal temperature of 90° C., followed by stirring at an internal temperature of 95 to 100° C. for 1.5 hours. After the completion of the reaction, the internal temperature was cooled to 50° C. or lower. Water was added to the reaction mixture, followed by extraction with 1,1,2-trichloroethane. The extract was washed successively with water and saturated saline and dried over magnesium sulfate. The solvent was then distilled off under reduced pressure. The resulting oil was distilled under reduced pressure (bp: 105 to 110° C., 3 mmHg), whereby 2-ethylthio-2,2,2', 4'-tetrafluoroacetophenone (4.6 g, yield: 35%) was obtained as a colorless oil.

$^1$H-NMR(CDCl$_3$, δ):
1.37(3H,t,J=7 Hz), 2.92(2H,q,J=7 Hz), 6.81–7.12(2H,m), 7.85–8.11(1H,m)

Example 2

Synthesis of 2-ethylthio-2,2,4'-trifluoroacetophenone [Compound (2-2)]

In a similar manner to Example 1 except for the use of 2-ethylthio-4'-fluoroacetophenone instead of 2-ethylthio-2', 4'-difluoroacetophenone, 2-ethylthio-2,2,4'-trifluoroacetophenone was obtained as a colorless oil.

$^1$H-NMR (CDCl$_3$, δ):
1.38(3H,t,J=7.5 Hz), 2.93(2H,q,J=7.5 Hz), 7.76(2H,d,J=8.6 Hz), 8.24(2H,d,J=8.6 Hz).

Example 3

Synthesis of 2-ethylthio-2,2-difluoro-4'-(trifluoromethyl)acetophenone [Compound (2-3)]

In a similar manner to Example 1 except for the use of 2-ethylthio-4'-trifluoromethylacetophenone instead of 2-ethylthio-2', 4'-difluoroacetophenone, 2-ethylthio-2,2-difluoro-4'-(trifluoromethyl)acetophenone was obtained as a colorless oil.

$^1$H-NMR(CDCl$_3$, δ):
1.38(3H,t,J=7.5 Hz), 2.94(2H,q,J=7.5 Hz), 7.00–7.40(2H, m), 8.0–8.4(2H,m)

Example 4

Synthesis of 2', 4'-dichloro-2-ethylthio-2,2-difluoroacetophenone [Compound (2-4)]

In a similar manner to Example 1 except for the use of 2', 4'-dichloro-2-(ethylthio)acetophenone instead of 2-ethylthio-2', 4'-difluoroacetophenone, 2', 4'-dichloro-2-ethylthio-2,2-difluoroacetophenone was obtained as a colorless oil.

$^1$H-NMR(CDCl$_3$, δ):
1.37(3H,t,J=7.7 Hz), 2.90(2H,q,J=7.7 Hz), 6.81–7.12(2H, m), 7.20–7.80(2H,m)

Example 5

Synthesis of 2-(2,4-difluorophenyl)-2-[(ethylthio)(difluoro)methyl]oxirane [Compound (3-1)]

A suspension of 60% NaH (876 mg, 0.022 mol) in THF (30 ml) - DMSO (50 ml) was heated to an external temperature of 50° C., followed by the addition of trimethylsulfoxonium iodide (4.8 g, 0.022 mol) in portions. After stirring at the same temperature for one hour, the reaction mixture was cooled to −20° C. and added dropwise with a solution of 2-ethylthio-2,2,2', 4'-tetrafluoroacetophenone (4.6 g, 0.018 mol) in THF (20 ml). The resulting mixture was stirred at room temperature for 2 hours. The reaction mixture was then poured into ice water, followed by extraction with ethyl acetate. The extract was washed successively with water and saturated saline and dried over magnesium sulfate. The solvent was then distilled off under reduced pressure, whereby 2-(2,4-difluorophenyl)-2-[(ethylthio) (difluoro) methyl]oxirane (4.3 g, yield: 90.0%) was obtained as a pale yellow oil.

$^1$H-NMR (CDCl$_3$, δ):
1.30(3H,t,J=7 Hz), 2.86(2H,q,J=7 Hz), 2.95–2.98(1H,m), 3.48(1H,d,J=5 Hz), 6.71–7.02(2H,m), 7.40–7.66(1H, m).

Example 6

Synthesis of 2-[(ethylthio)(difluoro)methyl]-2-(4-fluorophenyl)oxirane [Compound (3-2)]

In a similar manner to Example 5 except for the use of 2-ethylthio-2,2,4'-trifluoroacetophenone instead of 2-ethylthio-2,2,2', 4'-tetrafluoroacetophenone, 2-[(ethylthio)(difluoro)methyl]-2-(4-fluorophenyl)oxirane was obtained as a pale yellow oil.

$^1$H-NMR(CDCl$_3$δ):
1.30(3H,t,J=7.5 Hz), 2.86(3H,m), 3.46(1H,d,J=5.5 Hz), 6.80–7.30(2H,m), 7.40–7.70(2H,m).

Example 7

Synthesis of 2-[(ethylthio)(difluoro)methyl]-2-(4-trifluoromethylphenyl)oxirane [Compound (3—3)]

In a similar manner to Example 5 except for the use of 2-ethylthio-2,2-difluoro-4'-(trifluoromethyl)acetophenone instead of 2-ethylthio-2,2,2', 4'-tetrafluoroacetophenone, 2-[(ethylthio)(difluoro)methyl]-2-(4-trifluoromethylphenyl)oxirane was obtained as a pale yellow oil.

$^1$H-NMR(CDCl$_3$δ)
1.31(3H,t,J=7.5 Hz), 2.60–3.00(3H,m), 3.50(1H,d,J=5.5 Hz), 6.80–7.30(2H,m), 7.66(4H,br.s).

Example 8

Synthesis of 2-(2,4-dichlorophenyl)-2-[(ethylthio)(difluoro)methyl]oxirane [Compound (3-4)]

In a similar manner to Example 5 except for the use of 2-ethylthio-2', 4'-dichloro-2,2-difluoroacetophenone instead of 2-ethylthio-2,2,2', 4'-tetrafluoroacetophenone, 2-(2,4-dichlorophenyl)-2-[(ethylthio)(difluoro)methyl]oxirane was obtained as a pale yellow oil.

$^1$H-NMR(CDCl$_3$, δ):
1.30(3H,t,J=7.5 Hz), 2.60–3.10(3H,m), 3.58(1H,d,J=5.1 Hz), 6.80–7.30(2H,m), 7.20–7.60(3H,m).

Example 9

Synthesis of 2-(2,4-difluorophenyl)-1-(ethylthio)-1,1-difluoro-3-(1H-1,2,4-triazol-1-yl)-2-propanol [Compound (1a–1)]

To a solution of 2-(2,4-difluorophenyl)-2-[(ethylthio) (difluoro)methyl]oxirane (4.3 g, 0.016 mol) in DMSO (50 ml), 1,2,4-triazole (2.98 g, 0.043 mol) and potassium carbonate (5.96 g, 0.043 mol) were added, followed by stirring at 60° C. for 2 hours. After the completion of the reaction, water was added to the reaction mixture. The resulting mixture was extracted with ethyl acetate. The extract was washed successively with water and saturated saline and dried over magnesium sulfate. The solvent was then distilled off under reduced pressure. The residue so obtained was crystallized from isopropyl ether—ethyl acetate, whereby 2-(2,4-difluorophenyl)-1-(ethylthio)-1,1-difluoro-3-(1H-1, 2,4-triazol-1-yl)-2-propanol (1.5 g, yield: 25%) was obtained as colorless crystals.

Melting point: 109 to 110° C.
IR(KBr) $V_{max}$cm$^{-1}$: 3136, 1681, 1499, 1145
MS(FAB): 336(M+H)
$^1$H-NMR(CDCl$_3$, δ):
1.29(3H,t,J=7 Hz), 2.84(2H,q,J=7 Hz), 4.79(1H,d,J=14 Hz), 5.28(1H,d,J=14 Hz), 5.74(1H,s), 6.60–6.95(2H, m), 7.60–7.87(1H,m), 7.79(1H,s), 8.09(1H,s).

Example 10

Synthesis of 1-(ethylthio)-1,1-difluoro-2-(4-fluorophenyl)-3-(1H-1,2,4-triazol-1-yl)-2-propanol [Compound (1a–2)]

In a similar manner to Example 9 except for the use of 2-[(ethylthio)(difluoro)methyl]-2-(4-fluorophenyl)oxirane instead of 2-(2,4-difluorophenyl)-2-[(ethylthio)(difluoro)methyl]oxirane, 1-(ethylthio)-1,1-difluoro-2-(4-fluorophenyl)-3-(1H-1,2,4-triazol-1-yl)-2-propanol was obtained as colorless crystals.
Melting point: 101 to 102° C.
IR(KBr) $V_{max}$cm$^{-1}$: 3111, 1584, 1519, 1144
MS(FAB): 318(M+H)
$^1$H-NMR(CDCl$_3$, δ)
1.27(3H,t,J=7.5 Hz), 2.80(2H,q,J=7.5 Hz), 4.78(1H,d,J=14.5 Hz), 4.90(1H,d,J=14.5 Hz), 5.72(1H,s), 6.85–7.10 (2H,m), 7.40–7.70(1H,m), 7.77(1H,s), 7.93(1H,s).

Example 11

Synthesis of 1-(ethylthio)-1,1-difluoro-2-(4-trifluoromethylphenyl)-3-(1H-1,2,4-triazol-1-yl)-2-propanol [Compound (1a–3)]

In a similar manner to Example 9 except for the use of 2-[(ethylthio)(difluoro)methyl]-2-(4-trifluoromethylphenyl)oxirane instead of 2-(2,4-difluorophenyl)-2-[(ethylthio)(difluoro)methyl]oxirane, 1-(ethylthio)-1,1-difluoro-2-(4-trifluoromethylphenyl)-3-(1H-1,2,4-triazol-1-yl)-2-propanol was obtained as colorless crystals.
Melting point: 122 to 123° C.
IR(KBr) $V_{max}$cm$^{-1}$: 3207, 1620, 1514, 1121
MS(FAB): 368(M+H)
$^1$H-NMR(CDCl$_3$, δ):
1.27(3H,t,J=7.5 Hz), 2.81(2H,q,J=7.5 Hz), 4.72(1H,d,J=14.5 Hz), 4.95(1H,d,J=14.5 Hz), 5.41(1H,s), 7.58(2H, d,J=9.2 Hz), 7.70(2H,d,J=9.2 Hz), 7.87(1H,s), 7.95 (1H,s).

Example 12

Synthesis of 2-(2,4-dichlorophenyl)-1-(ethylthio)-1,1-difluoro-3-(1H-1,2,4-triazol-1-yl)-2-propanol [Compound (1a–4)]

In a similar manner to Example 9 except for the use of 2-(2,4-dichlorophenyl)-2-[(ethylthio)(difluoro)methyl]-oxirane instead of 2-(2,4-difluorophenyl)-2-[(ethylthio)(difluoro)methyl]oxirane, 2-(2,4-dichlorophenyl)-1-(ethylthio)-1,1-difluoro-3-(1H-1,2,4-triazol-1-yl)-2-propanol was obtained as colorless crystals.
Melting point: 98 to 100° C.
IR(KBr) $v_{max}$cm$^{-1}$: 3112, 1614, 1519, 1108
MS(FAB) : 368(M+H)
$^1$H-NMR(CDCl$_3$, δ):
1.30(3H,t,J=7.5 Hz), 2.85(2H,q,J=7.5 Hz), 4.85(1H,d,J=14.3 Hz), 5.82(1H,d,J=14.5 Hz), 5.91(1H,s), 7.05–7.30 (2H,m), 7.82(1H,s), 7.89(1H,d,J=8.6 Hz), 8.20(1H,s).

Example 13

Synthesis of 1-[2-(2,4-difluorophenyl)-3-ethylthio-3,3-difluoro-2-methoxypropyl]-1H-1,2,4-triazole [Compound (1a–5)]

To a solution of 60% sodium hydride (0.16 g, 4.0 mmol) in N,N-dimethylformamide (50 ml), 2-(2,4-difluorophenyl)-1-(ethylthio)-1,1-difluoro-3-(1H-1,2,4-triazole-1-yl)-2-propanol (1.0 g, 3.0 mmol) was added dropwise under ice cooling, followed by stirring at room temperature for 30 minutes. Methyl iodide (0.56 g, 3.9 mmol) was then added dropwise to the reaction mixture under ice cooling and the resulting mixture was stirred at room temperature for 1 hour. Water was added to the reaction mixture, followed by extraction with ether. The ether solution was washed with water and dried over sodium sulfate. The solvent was then distilled off under reduced pressure. The residue was subjected to a silica gel column and from the chloroform eluate fraction, 1-[2-(2,4-difluorophenyl)-3-ethylthio-3,3-difluoro-2-methoxypropyl]-1H-1,2,4-triazole (0.81 g, yield: 78%) was obtained as a colorless oil.
MS(FAB) : 350(M+H)
$^1$H-NMR(CDCl$_3$, δ):
1.29(3H,t,J=7.5 Hz), 2.82(2H,q,J=7.5 Hz), 3.70 –3.74 (3H,m), 5.10(2H,br.s), 6.6–6.9(1H,m), 7.4–7.7(1H,m), 7.80(1H,s), 8.00(1H,s).

Example 14

Synthesis of 1-[2-(benzyloxy)-2-(2,4-difluorophenyl)-3-(ethylthio)-3,3-difluoropropyl]-1H-1,2,4-triazole [Compound (1a–6)]

In a similar manner to Example 13 except for the use of benzyl chloride instead of methyl iodide, 1-[2-(benzyloxy)-2-(2,4-difluorophenyl)-3-(ethylthio)-3,3-difluoropropyl]-1H-1,2,4-triazole was obtained as a colorless oil.
MS(FAB) : 426(M+H)
$^1$H-NMR(CDCl$_3$, δ)
1.31(3H,t,J=7.3 Hz), 2.85(2H,q,J=7.3 Hz), 4.8–5.3(4H, m), 6.6–6.9(2H,m), 7.2–7.6(6H,m), 7.78(1H,s), 7.94 (1H,s).

Example 15

Synthesis of 2-(2,4-difluorophenyl)-1-(ethylsulfonyl)-1,1-difluoro-3-(1H-1,2,4-triazole-1-yl)-2-propanol [Compound (1c–1)]

To a solution of 2-(2,4-difluorophenyl)-1-(ethylthio)-1,1-difluoro-3-(1H-1,2,4-triazol-1-yl)-2-propanol (850 mg, 2.39 mmol) in dichloromethane (100 ml), 85% m-chloroperbenzoic acid (1.4 g, 5.75 mmol) was added at room temperature, followed by stirring at room temperature for 12 hours. After the completion of the reaction, a saturated aqueous solution of sodium thiosulfate and a saturated aqueous solution of sodium bicarbonate were added and the resulting mixture was stirred. The dichloromethane solution was separated and after washing with water, dried over magnesium sulfate. The solvent was then distilled off under reduced pressure. The residue so obtained was crystallized from isopropyl ether—ethyl acetate, whereby 2-(2,4-difluorophenyl)-1-(ethylsulfonyl)-1,1-difluoro-3-(1H-1,2,4-triazol-1-yl)-2-propanol (718 mg, yield: 78%) was obtained as colorless crystals.
Melting point: 117 to 118° C.
IR(KBr) $v_{max}$cm$^{-1}$: 3136, 1617, 1503, 1323

MS(FAB): 368(M+H)

¹H-NMR(CDCl₃, δ):

1.48(3H,t,J=7 Hz), 3.41(2H,q,J=7 Hz), 5.14(1H,d,J=14 Hz), 5.37(1H,d,J=14 Hz), 6.11(1H,s), 6.64–6.96(2H, m), 7.55–7.82(1H,m), 7.77(1H,s), 8.07(1H,s).

Example 16

Synthesis of 1-(ethylsulfonyl)-1,1-difluoro-2-(4-fluoro-phenyl)-3-(1H-1,2,4-triazol-1-yl)-2-propanol [Compound (1c–2)]

In a similar manner to Example 15 except for the use of 1-(ethylthio)-1,1-difluoro-2-(4-fluorophenyl)-3-(1H-1,2,4-triazol-1-yl)-2-propanol instead of 2-(2,4-difluorophenyl)-1-(ethylthio)-1,1-difluoro-3-(1H-1,2,4-triazol-1-yl)-2-propanol, 1-(ethylsulfonyl)-1,1-difluoro-2-(4-fluoro-phenyl)-3- (1H-1,2,4-triazol-1-yl)-2-propanol was obtained as colorless crystals.

Melting point: 82 to 84° C.

IR(KBr) $v_{max}$cm⁻¹: 3110, 1587, 1518, 1332

MS(FAB): 350(M+H)

¹H-NMR(CDCl₃, δ):

1.46(3H,t,J=7.5 Hz), 3.35(2H,q,J=7.5 Hz), 4.83(1H,d,J= 14.5 Hz), 5.27(1H,d,J=14.5 Hz), 5.81(1H,br.s), 6.90–7.10(2H,m), 7.30–7.60(2H,m), 7.80(1H,s), 7.90 (1H,s).

Example 17

Synthesis of 1-(ethylsulfonyl)-1,1-difluoro-2-(4-trifluoromethylphenyl)-3-(1H-1,2,4-triazol-1-yl)-2-propanol [Compound (1c–3)]

In a similar manner to Example 15 except for the use of 1-(ethylthio)-1,1-difluoro-2-(4-trifluoromethylphenyl)-3-(1H-1,2,4-triazol-1-yl)-2-propanol instead of 2-(2,4-difluorophenyl)-1-(ethylthio)-1,1-difluoro-3-(1H-1,2,4-triazol-1-yl)-2-propanol, 1-(ethylsulfonyl)-1,1-difluoro-2-(4-trifluoromethylphenyl)-3-(1H-1,2,4-triazol-1-yl)-2-propanol was obtained as colorless crystals.

Melting point: 155 to 157° C.

IR(KBr) $v_{max}$cm−1: 3207, 1620, 1514, 1329

MS(FAB) : 400(M+H)

¹H-NMR(CDCl₃, δ)

1.47(3H,t,J=7.5 Hz), 3.38(2H,q,J=7.5 Hz), 4.88(1H,d,J= 14.3 Hz), 5.32(1H,d,J=14.3 Hz), 6.09(1H,br.s), 7.64 (4H,s), 7.78(1H,s), 7.92(1H,s).

Example 18

Synthesis of 2-(2,4-dichlorophenyl)-1-(ethylsulfonyl)-1,1-difluoro-3-(1H-1,2,4-triazol-1-yl)-2-propanol [Compound (1c–4)]

In a similar manner to Example 15 except for the use of 2-(2,4-dichlorophenyl)-1-(ethylthio)-1,1-difluoro-3-(1H-1, 2,4-triazol-1-yl)-2-propanol instead of 2-(2,4-difluorophenyl)-1-(ethylthio)-1, 1-difluoro-3-(1H-1,2,4-triazol-1-yl)-2-propanol, 2-(2,4-dichlorophenyl)-1-(ethylsulfonyl)-1, 1-difluoro-3-(1H-1,2,4-triazol-1-yl)-2-propanol was obtained as colorless crystals.

Melting point: 79 to 81° C.

IR(KBr) $v_{max}$cm⁻¹: 3421, 1617, 1518, 1331

MS(FAB): 400(M+H)

¹H-NMR(CDCl₃, δ):

1.50(3H,t,J=7.7 Hz), 3.43(2H,q,J=7.7 Hz), 5.20(1H,d,J= 14.7 Hz), 6.13(1H,d,J=14.7 Hz), 6.31(1H,br.s), 7.10–7.40(2H,m), 7.88(1H,s), 7.74(1H,d,J=8.1 Hz), 8.16(1H,s).

Example 19

Synthesis of 1-[2-(2,4-difluorophenyl)-3-ethylsulfonyl-3,3-difluoro-2-methoxypropyl]-1H-1, 2,4-triazole [Compound (1c–5)]

In a similar manner to Example 15 except for the use of 1-[2-(2,4-difluorophenyl)-3-ethylthio-3,3-difluoro-2-methoxypropyl]-1H-1,2,4-triazole instead of 2-(2,4-difluorophenyl)-1-(ethylthio)-1,1-difluoro-3-(1H-1,2,4-triazol-1-yl)-2-propanol, 1-[2-(2,4-difluorophenyl)-3-ethylsulfonyl-3,3-difluoro-2-methoxypropyl]-1H-1,2,4-triazole was obtained as a colorless oil.

MS(FAB): 382(M+H)

¹H-NMR(CDCl₃, δ):

1.43(3H,t,J=7.5 Hz), 3.20(2H,q,J=7.5 Hz), 3.75(3H,br.s), 5.15(1H,d,J=5.5 Hz), 5.24(1H,d,J=5.5 Hz), 6.6–7.0 (2H,m), 7.4–7.7(1H,m), 7.78(1H,s), 8.06(1H,s).

Example 20

Synthesis of 1-[2-(benzyloxy)-2-(2,4-difluorophenyl)-3-(ethylsulfonyl)-3,3-difluoropropyl]-1H-1,2,4-triazole [Compound (1c–6)]

In a similar manner to Example 15 except for the use of 1-[2-(benzyloxy)-2-(2,4-difluorophenyl)-3-(ethylthio)-3,3-difluoropropyl]-1H-1,2,4-triazole instead of 2-(2,4-difluorophenyl)-1-(ethylthio)-1,1-difluoro-3-(1H-1,2,4-triazol-1-yl)-2-propanol, 1-[2-(benzyloxy)-2-(2,4-difluorophenyl)-3-(ethylsulfonyl)-3,3-difluoropropyl]-1H-1,2,4-triazole was obtained as a colorless oil.

(FAB) : 458 (M+H)

¹H-NMR(CDCl₃, δ):

1.41(3H,t,J=7.3 Hz), 3.19(2H,q,J=7.3 Hz), 5.07(2H,s), 5.27(1H,d,J=15.8 Hz), 5.50(1H,d,J=15.8 Hz), 6.6–7.0 (2H,m), 7.2–7.7(6H,m), 7.80(1H,s), 8.03(1H,s).

Example 21

Optical resolution of 2-(2,4-difluorophenyl)-1-(ethylsulfonyl)-1,1-difluoro-3-(1H-1,2,4-triazol-1-yl)-2-propanol [Compound (1c–1)] by using a column for the separation of an optically active substance 2-(2,4-Difluorophenyl)-1-(ethylsulfonyl)-1,1-difluoro-3-(1H-1,2, 4-triazol-1-yl)-2-propanol (40 mg) was subjected to CHIRALCEL OD (trade name; product of Daicel Chemical Industries, Ltd.), that is, a column for the separation of an optically active substance. From the eluate fraction of a 4:1 hexane—isopropyl alcohol mixture, 17 mg 2.0 (optical purity: 100% e.e.) of (+) form as colorless crystals and 17 mg (optical purity: 100% e.e.) of (−) form as colorless crystals were obtained in the order of elution. (1) (+)-2-(2, 4-difluorophenyl)-1-(ethylsulfonyl)-1,1-difluoro-3-(1H,1,2, 4-triazol-1-yl)-2-propanol $[\alpha]_D^{21.7}$+21.0°(C=0.1, acetone)

Melting point: 120 to 121° C.

IR(KBr) $v_{max}$cm⁻¹: 3136, 1617, 1503, 1323

MS(FAB): 368(M+H)

¹H-NMR(CDCl₃, δ):

1.48(3H,t,J=7 Hz), 3.41(2H,q,J=7 Hz), 5.14(1H,d,J=14 Hz), 5.37(1H,d,J=14 Hz), 6.11(1H,s), 6.64–6.96(2H, m), 7.55–7.82(1H,m), 7.77(1H,s), 8.07(1H,s).

(2) (−)-2-(2,4-difluorophenyl)-1-(ethylsulfonyl)-1,1-difluoro-3- (1H-1, 2, 4-triazol-1-yl)-2-propanol $[\alpha]_D^{21.7}$−21.5°(C=0.1, acetone)

Melting point: 120 to 121° C.

IR(KBr) $v_{max}$cm$^{-1}$: 3136, 1617, 1503, 1323

MS(FAB): 368(M+H)

$^1$H-NMR(DCDl$_3$, δ):

1.48(3H,t,J=7 Hz), 3.41(2H,q,J=7 Hz), 5.14(1H,d,J=14 Hz), 5.37(1H,d,J=14 Hz), 6.11(1H,s), 6.64–6.96(2H, m), 7.55–7.82(1H,m), 7.77(1H,s), 8.07(1H,s).

Example 22

Optical resolution of 1-(ethylsulfonyl)-1,1-difluoro-2-(4-fluorophenyl)-3-(1H-1,2,4-triazol-1-yl)-2-propanol [Compound (1c–2)] by using a column for the separation of an optically active substance In a similar manner to Example 21 except for the use of (±)-2-(4-fluorophenyl)-1-(ethylsulfonyl)-1,1-difluoro-3-(1H-1,2,4-triazol-1-yl)-2-propanol (220 mg) instead of (±)-1-(ethylsulfonyl)-1,1-difluoro-2-(2,4-difluorophenyl)-3-(1H-1,2,4-triazol-1-yl)-2-propanol, 100 mg (optical purity: 100% e.e.) of (+) form as colorless crystals and 100 mg (optical purity: 100% e.e.) of (−) form as colorless crystals were obtained in the order of elution. (1) (+)-1-(Ethylsulfonyl)-1,1-difluoro-2-(4-fluorophenyl)-3-(1H-1,2,4-triazol-1-yl)-2-propanol $[\alpha]_D^{20.6}$+23.0°(C=0.1, acetone)

Melting point: 131 to 132° C.

IR(KBr) $v_{max}$cm$^{-1}$: 3447, 1636, 1511, 1336

MS(FAB): 350(M+H)

$^1$H-NMR(CDCl$_3$, δ)

1.46(3H,t,J=7.5 Hz), 3.35(2H,q,J=7.5 Hz), 4.83(1H,d,J=14.5 Hz), 5.27(1H,d,J=14.5 Hz), 5.81(1H,br.s), 6.90–7.10(2H,m), 7.30–7.60(2H,m), 7.80(1H,s), 7.90 (1H,s).

(2) (−)-1-(Ethylsulfonyl)-1,1-difluoro-2-(4-fluorophenyl)-3-(1H-1,2,4-triazol-1-yl)-2-propanol $[\alpha]_D^{20.6}$+20.0° (C=0.1, acetone)

Melting point: 131 to 132° C.

IR(KBr) $v_{max}$cm$^{-1}$: 3447, 1636, 1511, 1336

MS (FAB): 350 (M+H)

$^1$H-NMR(CDCl$_3$, δ):

1.46(3H,t,J=7.5 Hz), 3.35(2H,q,J=7.5 Hz), 4.83(1H,d,J=14.5 Hz), 5.27(1H,d,J=14.5 Hz), 5.81(1H,br.s), 6.90–7.10(2H,m), 7.30–7.60(2H,m), 7.80(1H,s), 7.90 (1H,s).

Example 23

Preparation process of (−)-1-(ethylsulfonyl)-1,1-difluoro-2-(2,4-difluorophenyl)-3-(1H-1,2,4-triazol-1-yl)-2-propanol [Compound (1c–1)] by using a reagent for optical resolution In isopropyl alcohol (3.0 L), (+)-1-(ethylsulfonyl)-1,1-difluoro-2-(2,4-difluorophenyl)-3-(1H-1,2,4-triazol-1-yl)-2-propanol (130 g) and (+)-3-bromocamphor-8-sulfonic acid (115.7 g) were dissolved under heating, followed by inoculation of seed crystals. The reaction mixture was allowed to stand at room temperature for 5 days. The crystals so precipitated were collected by filtration, whereby 135.8 g (optical purity: 56.7% e.e.) of a (+)-3-bromocamphor-8-sulfonate salt of (−)-1-(ethylsulfonyl)-1,1-difluoro-2-(2,4-difluorophenyl)-3-(1H-1,2,4-triazol-1-yl)-2-propanol were obtained as colorless crystals. Recrystallization of the crystals so obtained was repeated using isopropyl alcohol as a solvent, whereby 72.1 g (optical purity: 93.1% e.e.) of a (+)-3-bromocamphor-8-sulfonate salt of (−)-1-(ethylsulfonyl)-1,1-difluoro-2-(2,4-difluorophenyl)-3-(1H-1,2,4-triazol-1-yl)-2-propanol were obtained as colorless crystals. To the resulting salt, a 5% aqueous solution of sodium bicarbonate was added to make it alkaline, followed by extraction with ethyl acetate. The extract was washed with water and dried. The solvent was then distilled off under reduced pressure. The residue was recrystallized from ethyl acetate—ether, whereby 41.4 g (optical purity: 99.7% e.e.) of (−)-1-(ethylsulfonyl)-1,1-difluoro-2-(2,4-difluorophenyl)-3-(1H-1,2,4-triazol-1-yl)-2-propanol were obtained as colorless crystals.

Test 1: Action against *Candida albicans* (in vitro)

To each well of a 96-well microtiter plate, 75 μl of a dilute medicament solution adjusted with a 10% fetal-bovine-serum added MEM medium (containing glutamine and a carbonate) were poured, followed by the addition of 75 μl of $4 \times 10^4$ cells/ml of *C. albicans* ATCC 44859 suspended in the same medium. The resulting mixture was incubated at 37° C. for 24 hours in a CO gas incubator. After incubation, a morphological change of *C. albicans* was observed under an inverted micro-scope. The minimum medicament concentration permitting the apparent suppression of mycerial type growth compared with that of a medicament-free control was designated as a terminal point (ng/ml). Incidentally, as a medicament for comparison, Fluconazole and known compound A ((−) -compound (1c–1) in Japanese Patent Application Laid-Open No. HEI 9-227531) were employed. The results are shown in Table 1.

Test 2: Action against *Aspergillus fumigatus* (in vitro)

To each well of a 96-well microtiter plate, 100 μl of a dilute medicament solution adjusted with 0.165M MOPS-containing RPMI 1640 medium (containing glutamine and phenol red, carbonate free; pH 7) were poured, followed by the addition of 100 μl of $6.0 \times 10^4$ conidia/ml of an *A. fumigatus* IFM 40808 spore suspension in the above medium containing 20% almar Blue. They were incubated at 35° C. for 48 hours. Judgment was made visually and the minimum medicament concentration not permitting a change into red (the medium maintained blue color) was designated as an MIC value (μg/ml). Incidentally, as a medicament for comparison, Fluconazole and known compound A ((−)-compound (1c–1) in Japanese Patent Application Laid-Open No. HEI 9-227531) were employed. The results are shown in Table 1.

TABLE 1

| Test compound | Terminal point (ng/ml) C. albicans | MIC (μg/ml) A. fumigatus |
|---|---|---|
| Example 9 | 7.8 | 2 |
| Example 10 | 31.3 | 8 |
| Example 11 | 7.8 | 16 |
| Example 12 | 3.9 | 1 |
| Example 13 | 31.3 | 8 |
| Example 15 | 31.3 | 8 |
| Example 18 | 15.6 | 8 |
| Example 21(2) | 15.6 | 4 |
| Example 22(2) | 15.6 | 8 |
| Fluconazole | 250 | >128 |
| Known compound A | 62.5 | 16 |

Test 3: Action against *Candida albicans* (in vivo)

After 4-week-old, male, ICR (CRJ: CD-1) mice were fasted for 6 hours, C. albicans IFM 40009 was inoculated to the tail vein of each of the mice to give an amount of $3.0 \times 10^6$ cells/mouse, whereby infection was caused. A control group consisted of 11 mice, while a medicament-administered group consisted of 5 mice. The medicament dissolved in 20% polyethylene glycol was orally administered 1 hour after the inoculation of the fungus and then consecutively once a day 24 hours after the inoculation, four times in total, at 1.25 mg/kg each. The survival condition on Day 14 after the infection was compared. In addition, the survival days of the control group and the medicament-administered group were detected by the Kaplan-Meier method (Cox mantel test). Incidentally, Fluconazole was employed as a medicament for comparison. The results are shown in Table 2.

TABLE 2

| Test compound | Average Survival days | Surviving mice on Day 14 number of surviving mice/total number in group |
|---|---|---|
| Example 15 | 14.00*** | 4/5 |
| Fluconazole | 11.0*** | 1/5 |
| Control | 4.5 | 0/11 |

(relative to control: ***p < 0.001)

Formulation examples will next be described. Example 24: Tablets

| Compound of Example 21(2) | 50 mg |
|---|---|
| Crystalline cellulose | 50 mg |
| Lactose | 50 mg |
| Hydroxypropyl cellulose | 18 mg |
| Magnesium stearate | 2 mg |
| Total | 170 mg |

In a conventional manner, tablets having the above-described composition were prepared. The tablets could be formed as sugar coated tablets or film coated tablets. Example 25: Capsules

| Compound of Example 21(2) | 50 mg |
|---|---|
| Light silicic anhydride | 25 mg |
| Lactose | 100 mg |
| Starch | 50 mg |
| Talc | 25 mg |
| Total | 250 mg |

The above ingredients were filled in No. 1 capsules, whereby capsules were obtained. Example 26: Granules

| Compound of Example 21(2) | 50 mg |
|---|---|
| Lactose | 600 mg |
| Corn starch | 200 mg |
| Carboxymethyl cellulose sodium | 20 mg |
| Hydroxypropyl cellulose | 130 mg |
| Total | 1000 mg |

In a conventional manner, granules having the above-described composition were prepared. Example 27: Powders

| Compound of Example 21(2) | 50 mg |
|---|---|
| Light silicic anhydride | 20 mg |
| Precipitated calcium carbonate | 10 mg |
| Lactose | 250 mg |
| Starch | 70 mg |
| Total | 400 mg |

In a conventional manner, powders having the above-described composition were prepared.

| Compound of Example 21(2) | 5 mg |
|---|---|
| Hydrogenated castor oil | 85 mg |
| Propylene glycol | 60 mg |
| Glucose | 50 mg |
| Distilled water for injection | q.s. |
| Total | 1 ml |

In a conventional manner, an injection having the above-described composition was prepared. Example 29: Intravenous drip infusion

| Compound of Example 21(2) | 50 mg |
|---|---|
| Hydrogenated castor oil | 5 g |
| Propylene glycol | 10 mg |
| Glucose | 14.5 mg |
| Distilled water for injection | q.s. |
| Total | 100 ml |

An intravenous drip infusion having the above-described composition was prepared in a conventional manner.

Japanese Patent Application Nos. 9-359202 filed on Dec. 26, 1997 and 10-186198 filed on Jul. 1, 1998, are incorporated herein by reference in its entirety.

What is claimed is:

1. A triazole derivative represented by the following formula (1):

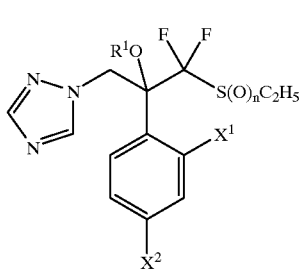

(1)

wherein $R^1$ represents a hydrogen atom, a lower alkyl group or a phenyl-$C_{14}$ group, $X^1$ and $X^2$ are the same or different and each independently represents a hydrogen atom, a halogen atom or a halogen (lower) alkyl group and n stands for an integer of 0 to 2, or salt thereof.

2. An antimycotic pharmaceutical composition comprising the triazole derivative or salt thereof as claimed in claim 1 and a pharmacologically acceptable carrier.

3. A treating method of mycotic infections, which comprises administering an effective amount of a triazole derivative or salt thereof as claimed in claim 1.

* * * * *